Figure 1:
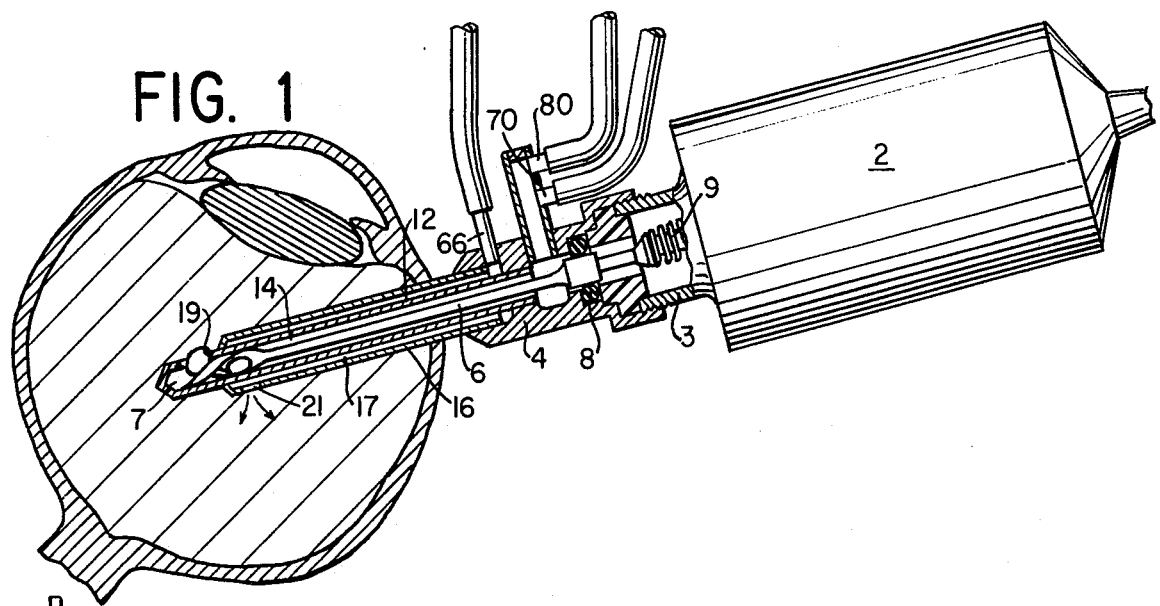

United States Patent [19]

Banko

[11] 4,007,742
[45] Feb. 15, 1977

[54] SURGICAL SYSTEM FOR CONTROLLING THE INFUSION OF FLUID TO AND THE EVACUATION OF FLUID AND MATERIAL FROM AN OPERATING FIELD

[75] Inventor: Anton Banko, Bronx, N.Y.

[73] Assignee: Surgical Design Corporation., Long Island City, N.Y.

[22] Filed: Nov. 17, 1975

[21] Appl. No.: 632,767

Related U.S. Application Data

[63] Continuation-in-part of Ser. No. 475,398, June 3, 1974, Pat. No. 3,920,014.

[52] U.S. Cl. .................................. 128/230; 128/276
[51] Int. Cl.² ......................................... A61M 1/00
[58] Field of Search .......... 128/230, 276, 277, 278, 128/2 A; 137/205

[56] References Cited
UNITED STATES PATENTS

| | | | |
|---|---|---|---|
| 2,646,042 | 7/1953 | Hu | 128/276 X |
| 3,429,313 | 2/1969 | Romanelli | 128/230 X |
| 3,513,846 | 5/1970 | Gallo | 128/276 X |
| 3,599,639 | 8/1971 | Spotz | 128/276 |
| 3,788,305 | 1/1974 | Schreiber | 128/276 X |
| 3,812,855 | 5/1974 | Banko | 128/276 X |
| 3,920,014 | 11/1975 | Banko | 128/230 |

*Primary Examiner*—John D. Yasko
*Attorney, Agent, or Firm*—Darby & Darby

[57] ABSTRACT

A system for controlling the infusion of fluid to an operating field at a selected predetermined pressure, as a counterpart to an instrument for severing material from an object in the field, and for evacuating the severed material from the field in a suspension or emulsion of the infusion fluid. The system includes a feature for preventing a low pressure in the operating field, to thereby prevent a surge of fluid from the field, when the evacuation function is terminated by equalizing the pressure in both the infusion and evacuation lines by supplying both lines with fluid from the same container.

8 Claims, 2 Drawing Figures

U.S. Patent    Feb. 15, 1977    4,007,742

SURGICAL SYSTEM FOR CONTROLLING THE INFUSION OF FLUID TO AND THE EVACUATION OF FLUID AND MATERIAL FROM AN OPERATING FIELD

This application is a continuation-in-part of my prior copending application Ser. No. 475,398 filed June 3, 1974 entitled SURGICAL SYSTEM FOR CONTROLLING THE INFUSION OF FLUID TO AND THE EVACUATION OF FLUID AND MATERIAL FROM AN OPERATING FIELD, now U.S. Pat. No. 3,920,014 granted Nov. 18, 1975, which is assigned to the same assignee.

This invention relates to a surgical apparatus and more particularly to an apparatus having particular utility in an operation taking place in a closed operating field, such as the eye of an animal or human being.

In my aforesaid patents, systems are disclosed for use in conjunction with a surgical instrument of the type which can remove material from an object, such as by cutting, drilling, emulsifying such as by using ultrasonic energy, tearing, etc. The systems operate to infuse fluid in an operating field for certain purposes, such as to maintain a predetermined pressure, and also for evacuating from the field the severed material removed from the object in suspension with or as an emulsion of the infusion fluid.

The present invention relates to a simplified system of the general type disclosed and claimed in the foregoing patents. The system of the subject invention is capable of performing a variety of functions all under the control of an operator. Among these are the supply of a fluid to the operating field at a predetermined pressure after the surgical instrument is located in the operating field. This is accomplished by a gravity flow arrangement for the infusion fluid in which the infusion fluid container is placed at a given height above the operating field. Maintaining the predetermined pressure keeps the operating field, for example the eye, formed in its normal physical shape both before and during the operation. During the operation the system also: (1) creates an evacuation flow for transportation of the material severed by the surgical instrument, which material is suspended or is emulsified in the supplied fluid and in the normal fluid of the operating field; (2) substitutes fluid to compensate for the volume of material, both solid and liquid, removed from the operating field; and (3) provides a pressure in the evacuation line when evacuation is stopped which is substantially the same as the pressure in the infusion line and operating field.

Function (3) described above is accomplished in accordance with the subject invention in a highly simplified manner by applying the infusion fluid to the evacuation portion of the instrument when the evacuation process has stopped. This prevents further motion of material from the operating field into the instrument and it also prevents the operating field from being emptied of material which would ultimately cause it to collapse.

The present invention operates to block the evacuation path during the time no material is being evacuated or the end distal to the evacuation mechanism (pump or syringe) is filled with viscous material of high resistance to motion through the evacuation line covering a differential pressure between the two ends of the line (the eye and the evacuation mechanism). This differential pressure would be eliminated by further motion of contents (fluid or tissue from the eye) and if this motion is greater than a possible (if available) infusion of substance into the eye the eye pressure would diminish and so would its volume causing portions of the eye to change their relative position to the evacuation post of the instrument jeopardizing the safety of these portions of the eye. If in such an event healthy tissue has inadvertently entered the evacuation port its removal would continue until the differential pressure in the line exists. The amount of substance being removed from the eye after the evacuation mechanism is stopped depends on the volume of the evacuation line, the elasticity of the line and the pressure within it. A combination of these factors may cause the eye to be emptied completely and instantaneously.

It is therefore an object of the present invention to provide a novel surgical system for controlling the infusion of fluid from an instrument to an operating field, and the evacuation of fluid and material from the operating field.

A further object is to provide a liquid infusion and material evacuating system for use in connection with a surgical instrument for removing material from an object in which the evacuation path is blocked during the time no material is being evacuated.

An additional object is to provide a system utilizing easily operated control members for controlling the infusion of fluid and the evacuation of fluid and material from an operating field.

Another object is to provide a liquid infusion and material evacuating system for use with a surgical instrument in which infusion fluid is supplied to the evacuation passage of the instrument during the time when no evacuation is taking place.

Figure 2:
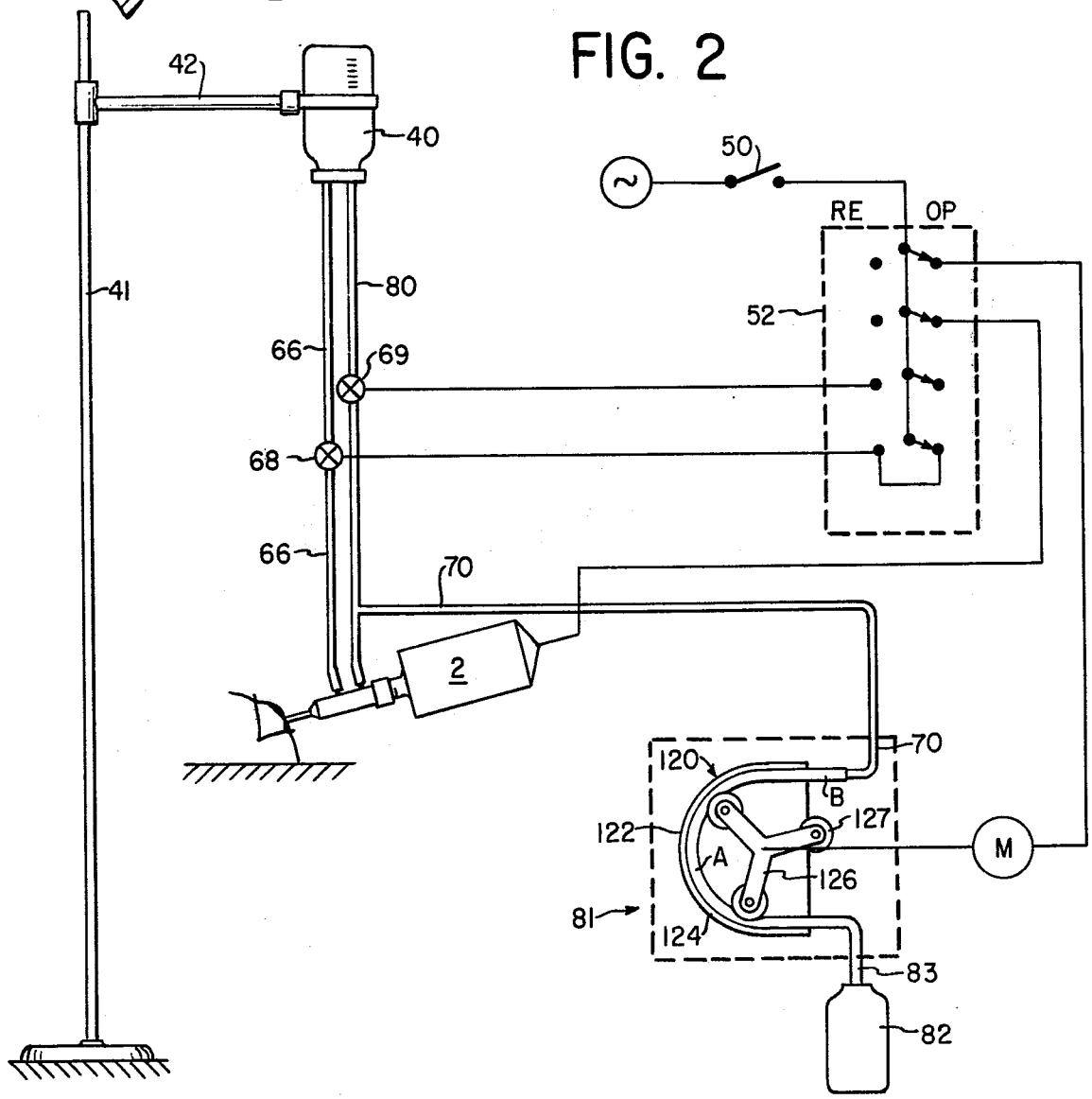

Other objects and advantages of the present invention will become more apparent upon reference to the following specification and annexed drawings, in which:

FIG. 1 is an overall plan view, taken partly in cross-section, of a typical instrument for use with the system of the present invention; and FIG. 2 is a combined schematic electrical and pneumatic line diagram showing the various components of the system and their operation.

Referring to the drawings, the system is described with respect to performing an operation on the eye of an animal or a human being. It should be understood, of course, that the system can be utilized with at any performance of operations and other types of environments.

FIG. 1 shows a typical surgical instrument 10 which can be used with the control system of the present invention. It should be understood, however, that the system can be used with any type of instrument or instrument set-up which requires pressurized flow of a liquid (infusion) and/or evacuation (suction) of fluid and severed material from an operating field. As indicated above, in the example being described the operating field is the eye. Instruments which can be used with the system includes various types of mechanical cutting, drilling, scraping or severing instruments as well as other instruments, for example those of the ultrasonic type, which emulsify material to be removed.

In the embodiment of the invention being described, the tip of instrument 10 is shown as having pierced through a section of the eye, for example after an incision has been made. The tip of the instrument is shown in the vitreous of the eye to remove tissue therefrom or to treat the eye. The instrument of FIG. 1 also can be used to remove material from other parts of the eye such as the lens, a cataract or iris. It should be understood that the system can be used with any compatible type of instrument to perform operations or treatment in any portion of the body of a mammal.

The instrument 10 of FIG. 1 includes an electric motor 2, preferably of the reversible type, from which extends a collar 3. A fitting 4 is screwed onto collar 3 and concentric inner and outer tubular members 12 and 16 extend from fitting 4. Inner tube 12 defines a central passage 14 through which evacuation takes place over a line 70, to be described below, which communicates with passage 14 through a coupling on fitting 4. The space between the inner and the outer tubes 12 and 16 defines a passage 17 through which infusion fluid is supplied over a line 66. The evacuation passage 14, can also be supplied infusion fluid through a line 80. Lines 70 and 80 communicate with passage 14 through a common coupling in fitting 4.

The inner, evacuation flow, member 12 of the instrument has an opening 19 at the end thereof through which the evacuation flow (suction) is applied to the operation field. The infusion flow member 16 has one or more openings 21 in its wall, spaced from and opposite to opening 19 to avoid interference, through which fluid is infused into the operating field. A shaft 6 having a fluted cutter 7 at the end thereof is located in the inner passage 14. The shaft is connected to the motor output and rotates in bearings (sealing element) 8 in the fitting 4. Shaft 6 is preferably biased by a spring 9 so that the cutter 7 will coact preferably in a manner with no clearance with the surface surrounding the evacuation opening 19 to produce a shearing action to cut any tissue therebetween. In operation, the tip of the instrument is moved to place the shearing opening 19 7 at the site of the material to be severed. The evacuation flow from opening 19 aids in drawing the material into a relationship so that it can be severed by the translating edge of cutter 7 and stationary edge of opening 19. The severed material, in suspension or as part of an emulsion, is drawn up passage 14 and is removed via line 70. Infusion fluid is supplied over line 66 to the eye through passage 17 and its opening 21. In addition, as described in greater detail below, infusion fluid also can be supplied to the evacuation passage 14 when the evacuation process wants to be terminated and the evacuation mechanism has stopped.

The system of the invention provides a selected predetermined pressure of infusion fluid in the operating field. In addition it equalizes the pressure between the infusion and evacuation passages when the evacuation process has to be stopped. This is described below.

FIG. 2 shows the fluid flow and electrical control system components of the system. The double lines indicate fluid flow paths and the single lines electrical connections. The infusion fluid supply for the instrument 10 is illustratively shown as a bottle 40 having a calibrated scale thereon to show the amount of fluid. In a typical case, saline solution is utilized as the fluid. The bottle 40 is held upside down on a stand 41 by a support 42 and the height of the bottle is adjustable with respect to the operating field, here the eye, by moving the support up and down. A height scale can be provided as the stand 41 and support and also as the operating table on which the patient is lying so that the relative distance between the operating field, where the instrument is located, and the container 60 can be controlled. In this manner, the pressure in the operating field is controlled. That is, the infusion fluid pressure in the operating field is determined by the height of the level of fluid in the container 60 relative to the operating field. The greater the height the greater will be the pressure and vice versa. The desired pressure during surgery in a closed operation in the eye is 15–30 mm Hg which will be provided by the height of 8–16 inches of fluid level above the eye.

Infusion line 66 is attached to a cap on the bottle 60 to receive fluid therefrom to be conveyed to the outer, infusion, passage 16 of the instrument 10. This is the infusion fluid to such passage. An electromechanically controlled valve 68 is located in line 66 between bottle 60 and the instrument to control the fluid flow. Line 66 also can be of vinyl, rubber or other suitable material.

Fluid line 80 also receives infusion fluid from the bottle 60. This is the pressure equalizing fluid-flow line whose outlet end is connected to the instrument 10 to supply fluid to the inner (evacuation) passage 16 of the instrument. An electromechanically operated valve 69 is located in line 80 between the bottle 60 and the outlet of flow line 80 to control the flow of fluid to the outlet.

The infusion flow rate depends upon the difference in pressure at the port 21 prior to and during the evacuation process. In general, in the case of an eye using a microsurgery type instrument, the drop in pressure during the evacuation process is about 2–5 mm Hg for each 1cc/min of material removed. This quantity is then replaced by infusion.

An evacuation mechanism 81 removes the severed or emulsified material from the eye through evacuation line 70 which is connected to the inner, evacuation, passage 14 of instrument 10. The evacuation mechanism preferably includes a peristaltic type pump, for example, the Master Flex Tubing Pump, Model 7013 made by Cole-Parmer Company, of Chicago, Ill. The operation of this type of pump is described in greater detail below. The evacuation is carried out at a substantially constant rate, which can be selected and present on the pump, to create a flow of material from the eye in a substantially gasless column of liquid. Line 80 empties into a waste bottle 82 through the pump and a line 83. The material emptied into bottle 82 includes fluid from the operating field together with the material severed from the object by the instrument.

The evacuation mechanism 81 operates to maintain a substantially constant evacuation flow in line 70. As indicated previously, the mechanism includes a constant displacement type pump, which in the preferred embodiment is a peristaltic pump 120. This has a hemispherical housing portion 122 of rigid material and a flexible plastic tubing 124 within the housing against which a triple arm roller system 126 rotates. The rollers 127 are spaced about 120° apart. The roller system 126 is rotated by a suitable conventional motor (not shown) whose speed can be controlled. The inlet to pump 120 is the evacuation line 70 which is preferably a rigid tubing of plastic, rubber or other suitable material. The outlet 83 of the pump is to the waste bottle 82.

The peristaltic pump 120 moves a column of liquid in a section A between two of its rollers 127, creating space for the contents of section B in tubing 70 between the instrument outlet and the closest roller 127 of pump 120 to the instrument. Rotation of the roller on the tubing in the pump 120 in area A creates a flow of material out of the pump exit passage 83. Fluid is being forced into the operating field at the same time over the infusion line and from the evacuation passage 14 of the instrument and line 70 up to the pump inlet.

When the peristaltic pump inlet is near the eye and the instrument is connected to the pump by a relatively short and rigid tube 70, then the displacement of fluid by the pump is communicated to the eye with negligible time delay imposed by a flow through the cutting opening 19 of the instrument.

As indicated previously, the incision is first made in the operating field and the instrument is then inserted. In addition to being "off" the system operates in two distinct modes which are described below. An "on-off" switch 50 connects the system to a power supply shown as an alternating current source. The switch is connected to a three pole, double throw switch 52 which can be, for example, a foot switch under the control of the operator. Switch 52 has two positions, "operate" and "release", preferably being spring based to rest in the release position.

1. Operating Mode — This mode is obtained by having the operator of the system operate the foot switch 52. This completes electric circuits to turn on both the motor for the evacuation mechanism 81 and to operate the electric motor of the instrument 2 to turn the cutter in the forward direction. Where other types of instruments are used, for example an ultrasonic probe or turbofragmentator, these would be energized at this time. At the same time, valve 68 in the infusion pressure line 66 is energized, opened and valve 69 in the pressure equalization line 80 is closed.

The rate of infusion fluid flow into the operating field depends on the rate of evacuation over line 70. The infusion fluid pressure is set by raising or lowering the bottle 60. The maximum incoming rate of infusion fluid is limited so as not to create prohibitive streaming and consequent undesired displacement of floating tissue and other substance as in the operating field, generally near and around the cutting opening 19 of the instrument 10. A high velocity of the incoming infusion liquid is desirably avoided since it has a mass impulse which may damage delicate tissue in the operating field.

Therefore, the maximum rate of inflow of the infusion fluid must be controlled and, in some cases, limited. To accomplish this the evacuating system should be set so as to prevent the evacuation from exceeding a rate such that the pressure in the operating field can be maintained without creating undesirably high inflow rates of the infusion fluid.

The pressure in the operating field is to be maintained within tolerable limits below a desired maximum level, usually less than 30-35 mm of Hg above the atmospheric pressure in the case of a normal operation on the eye. However, for example, in the case where there is bleeding in the eye, the pressure can be set to control the bleeding by increasing it to counteract the pressure of the blood being pumped by the heart. The evacuation system will also operate at higher pressure to remove the blood from the operating site permitting better visualization for cauterizing. If bleeding does not terminate spontaneously after the latter is done, the pressure is reduced and the operation continues at a lower pressure.

During the operating mode the material separated by the instrument cutter is entrained in suspension in the infusion fluid and is moved to the waste bottle 83 by the evacuation mechanism 81. The pressure in the evacuation line 80 depends on several factors. These are: (1) the cross section of the inlet opening to the instrument, this changes where there is a movable cutter; (2) the speed of the evacuation mechanism itself; and (3) the viscosity of the infusion fluid and the material being removed.

The pump 120 is normally set to rotate at a constant speed to create a desired flow rate of fluid through the eye. The flow resistance through the instrument opening 19 and the rest of the evacuation line 80 is changing continuously during the operation. When the resistance increases, a greater force is needed to move a slightly smaller amount of suspension by the pump (the tube 70 shrinks and volume A slightly decreases due to a lower pressure in portion B of the line). The flow rate decreases slightly through the instrument cutter opening as well. This occurs as the volume of portion B of the line 70 decreases (tubing shrinks) due to lower pressure inside generated by increased resistance at the instrument opening.

When the resistance at the opening 19 increases further and the pump is still moving at a set speed, evacuating the fluid suspension from volume B, then the pressure in volume B decreases further. If this process continues the column of liquid in portion of the tubing B will break and form spaces of low pressure vapors or even vacuum. And if there is any air or other gases dissolved in the suspension, they will start to separate and their volume will increase as pressure in volume B drops further.

So far no damage was done to the eye. Exit of the infusion solution is blocked, the eye is formed and its inside pressure is at its maximum desired level. If the resistance at the instrument opening would decrease slowly and gradually, which seldom happens, then the flow from the eye will resume and increase gradually until volume B is filled up again. The outflow from the eye is matched by the inflow so the eye stays formed. The flow will then stabilize at a slightly changing level. In a more typical case, the resistance decreases momentarily, e.g. because the instrument opening is unblocked, and the volume B, which was partially or totally empty, fills up in a short time. The flow out of the eye is then greater than the flow in the eye. Its maximum depends on the height of the container 60. The eye loses its desired pressure and it will soften and collapse. Also, portions of healthy tissue of the eye may enter the cutter opening of the instrument with disastrous effects.

To prevent this from occurring with the described system, it is imperative to prevent prohibitive reduction of volume or density of the fluid suspension in volume B of the evacuating line 70. This is achieved by keeping B small and its inside pressure relatively high. Short tubings with a small inner diameter will provide the small volume. The change in volume in relation to the original volume will be small if the tubing is made of rigid material (metal, or thick wall flexible plastic tubing, for example, TYGON).

When the critical pressure (at which cohesive forces in the liquid column are exceeded) is reached, the liquid column will break and liquid-less spaces can be noticed through the wall of a clear flexible plastic tubing. The pressure level at which this separation takes place depends on the consistency of the liquid suspension and its temperature, but it can be clearly established for a given case. This pressure level can be observed on a pressure (suction) gauge and the pump can be stopped before it reaches the undesired level. The liquid column will not break and gases will not separate if pressure in volume B is kept above a given level. This may be achieved by stopping the pump prior the critical pressure is reached.

Separation of gases from the liquid suspension is a third disturbing factor (the first, shrinkage of tubing, the second, breakage of liquid column). Gases dissolved in liquid can be separated at a given (room) temperature if pressure on and in the liquid is decreased. As before, when pressure in a clear elastic plastic tubing is sufficiently reduced, at first a small quantity of very small gas bubbles appear in the liquid and as pressure is further reduced the number and size of the bubbles increases. The pressure at which the separation starts to be apparent can be observed on a pressure gauge and if the pump is stopped before the pressure reaches the undesired value, the separation will not occur. If some small degree of separation occurs it will not be harmful in terms of the problem described.

In either case if breaking of the column or fluid or separation of gases, the evacuation mechanism 81 can be stopped manually or by releasing switch 52 if and when the observed conditions in portion of the line B visually appear to become critical. When, and if, the flow from the eye through the cutter opening 19 of the instrument resumes (or increases) the pressure in volume B will increase and the pump can be started again by moving the switch to the operate position.

2. Release Mode — The system goes into this mode at all times when it is on and it is not in the operating mode where material is being severed, or otherwise operated on, and moved into the evacuation. To produce this mode the instrument is on and the switch 52 is in the release position. The electrical circuitry is such that the motor for the cutter of instrument 10 is off as is the motor for the evacuation mechanism 81. At the same time, both the infusion line control valve 68 and the equilization pressure line control valve 69 are open.

When the evacuation mechanism is stopped, there would still be a pressure differential between the evacuation passage 19 and the end portion B of the pump until the evacuation line 80 is filled completely from the contents of the eye. There would be a tendency to pull material at the proximity of and in passage 19 into the evacuation line. It is not normally desirable to block the flow of infusion fluid during the release mode since this might cause a pressure build up through the evacuation channel 14 causing a reverse of flow of the material already removed from the operating field into the eye.

All of the foregoing disadvantages are eliminated by the system of the present invention wherein infusion fluid is provided to both the infusion and evacuation passages when the system goes into the ready mode. As seen, with the opening of valve 69 the infusion fluid is applied over the pressure equalization line 80 to the evacuation passage. Since the pressure in both the infusion and evacuation passage is the same there is an equalization and no material can flow into or from the evacuation passage after the equilibrium is achieved. The operating field continuously receives infusion fluid continuously from 19 and 21 so that any leakage is compensated for and the field stays properly formed. It should be understood that the pressure in the operating field can never exceed the pressure of the infusion fluid which is determined by the height of container 60. The latter is selected to set the pressure at a safe level.

As should be apparent a novel system has been disclosed for use with an instrument of the type which is for removing material from an operating field in which a simple but highly effective arrangement prevents material outflow and other unwanted effects when the system is in the release mode of operation.

While the aspect of the invention relating to the application of the infusion fluid to the evacuation passage hs been shown in connection with a gravity fed infusion fluid container, it should be understood that it is also applicable to a system wherein the infusion fluid container is pressurized, for example by a pump, such as shown in my U.S. Pat. No. 3,920,014.

If desired, the control valve 68 in the infusion line can be eliminated since, in the preferred embodiment disclosed, the infusion passage always receives fluid.

What is claimed is:

1. In combination, a system for use with a surgical instrument of the type having an operative portion at an operating site with the operative portion including a first means for delivering an infusion fluid to the operating site and a second means for removing material from the operating site,
    a source of infusion fluid,
    means for supplying infusion fluid from said source to said first means of said instrument,
    means producing a pressure differential condition at said second means of the instrument with respect to the pressure of the infusion fluid at said first means to provide removal of material from the operating site,
    means including first control means for selectively providing infusion fluid to said second means of said instrument,
    and means for selectively operating said pressure differential producing means and said first control means in first and second conditions wherein in the first condition material is removed by said second means of the instrument and infusion fluid is blocked from said second means by said first control means, and in a second condition wherein said removal of material by said second means is blocked and operates said first control means to supply infusion fluid to said second means of the instrument at the same time said first means is receiving infusion fluid.

2. The combination of claim 1 wherein said infusion fluid source supplies fluid to said first means by gravity flow.

3. The combination of claim 1 further comprising means for adjusting the pressure of the infusion fluid supplied by the source by adjusting the height of the source relative to the operating site.

4. The combination of claim 1 wherein said means producing the pressure differential condition and the first control means are electrically operated, said selectively operating means including electrical switching means for switching between said first and said second conditions.

5. The combination of claim 4 wherein said first control means comprises an electrically operated valve.

6. The combination of claim 1 wherein said instrument comprises first and second concentric tubular members of different diameters with the first means including the interior passage of one of said members and said second means including the passage between said two members, each of said members having an outlet, said supply means for the infusion fluid communicating fluid to one of said passages, and both said means for providing the differential pressure and the means for selectively applying the infusion fluid communicating with the other of said passages.

7. The combination of claim 6 wherein said means producing the pressure differential condition and the first control means are electrically operated, said selectively operating means including electrical switching means for switching between said first and said second conditions.

8. The combination of claim 7 wherein said first control means comprises an electrically operated valve.

* * * * *